United States Patent [19]

Yamada

[11] Patent Number: 5,054,486

[45] Date of Patent: Oct. 8, 1991

[54] REMEDIAL TECHNIQUES FOR THE TREATMENT OF PAINFUL DISORDERS SUCH AS INTERVERTEBRAL DISC HERNIA AND THE LIKE

[76] Inventor: Mamoru Yamada, 1-40-6, Toro-machi, Omiya City, Saitama Prefecture, Japan

[21] Appl. No.: 531,089

[22] Filed: May 31, 1990

[51] Int. Cl.⁵ ............................................. A61N 1/02
[52] U.S. Cl. ................................. 128/421; 128/907; 128/735; 606/13
[58] Field of Search ............... 128/421, 907, 395, 396, 128/397, 398, 422, 735; 606/10, 17, 16, 13

[56] References Cited

U.S. PATENT DOCUMENTS 3,897,789  8/1975  Blanchard .......................... 128/421
4,564,012  1/1986  Shimada et al. ..................... 128/395
4,844,069  7/1989  Mori .................................... 128/395
4,930,505  6/1990  Hatje ................................... 128/398

FOREIGN PATENT DOCUMENTS 2740969  3/1979  Fed. Rep. of Germany ...... 128/398

*Primary Examiner*—William E. Kamm
*Assistant Examiner*—Scott M. Getzow
*Attorney, Agent, or Firm*—Ronald P. Kananen

[57] ABSTRACT

Remedial techniques for the treatment of intervertebral disc hernia, stiff shoulders, rheumatics, allergy-related nasitis, lumbago, asthma, slipped disc, sprains and the like which do not require the use of drugs/medicines, comprise the individual or combined use of: a radicular block which is achieved by inserting an acupuncture needle into a selected radicular and passing a current between it and a ground (such as a second acupuncture needle); and a YAG laser irradiation technique wherein selected sites on the human body are irradiated for a preselected period.

12 Claims, 4 Drawing Sheets

REMEDIAL TECHNIQUES FOR THE TREATMENT OF PAINFUL DISORDERS SUCH AS INTERVERTEBRAL DISC HERNIA AND THE LIKE

BACKGROUND OF THE INVENTION

Field of the Invention

The present invention relates generally to remedial treatments for intervertebral disc hernia and the like type of painful and movement inhibiting malady.

SUMMARY OF THE INVENTION

It is an object of the present invention to provide a technique or techniques which do not require the use of drugs or medicines and which can provide very marked improvements in the symptoms exhibited by patients suffering from intervertebral disc hernia (ruptured discs) and the like type of painful and/or disabling disorders which interfere with free movement, normal work and/or daily duties.

It is a further object of the invention to provide a remedial technique or techniques of the above mentioned type which can be taught to, and executed competently by operators having badly to very badly impaired sight.

It is a further object of the present invention to provide techniques which can be used synergistically in combination to achieve alleviation of the symptoms associated with ruptured discs and the like type of malady.

In brief, the above objects are achieved by the individual or combined use of: a radicular block which is achieved by inserting an acupuncture needle into a selected radicular and passing a current between it and a ground (such as a second acupuncture needle); and a YAG laser irradiation technique wherein selected sites on the human body are irradiated for a preselected period.

More specifically, a first aspect of the present invention relates to remedial technique comprising the steps of: inserting an acupuncture needle into a preselected radicular of the patient's spinal cord; providing a ground by which electrical current applied to the patient's body through the needle can be grounded; and applying a pulsed electrical current across the needle and the ground until the preselected radicular is blocked.

A second aspect of the present invention is deemed to comprise a remedial technique comprising the steps of: irradiating a predetermined location of a patient's body using a laser beam for a given length of time; and repeating the irradiation at a plurality of other locations until such time as the patient experiences a deep warming sensation over the area under treatment.

A third aspect of the present invention is deemed to relate to a remedial apparatus comprising: a laser source; a hand held applicator, the hand-held applicator having a contact portion which can be placed directly in contact with the skin of a human body; a flexible light conducting fiber cable which operatively interconnects the laser source and the hand-held applicator; and lens means included in the hand-held applicator for focussing the laser at a point which is located at a predetermined distance from the contact portion and such that when the hand-held applicator is placed against the skin of a human body, the cross-sectional area of the laser beam which is irradiated on the skin of the human body is relatively large and prevents the tendency for the beam to burn the skin.

A further aspect of the present invention relates to the form of a remedial technique comprising the steps of: inserting an acupuncture needle into a preselected radicular of the patient's spinal cord; providing a ground via which electrical current applied to the patient's body can be grounded; applying a pulsed electrical current across the needle and the ground until the preselected radicular is blocked; irradiating a predetermined location of a patient's body proximate the site of the radicular block using a laser beam for a given length of time; and repeating the irradiation at a plurality of other locations until such time as the patient experiences a deep warming sensation over the area under treatment.

DETAILED DESCRIPTION OF THE PREFERRED EMBODIMENTS

A first aspect of the present invention relates to a radicular blocking technique. This first aspect involves blocking one or more radicular which are associated with the pain or malady a patient is experiencing. This is done by inserting a suitable acupuncture needle "n" into a radicular of the spinal cord, providing a suitable ground "g" such as a second acupuncture needle or conductive plate, and then applying a pulsed electrical signal from a suitable source "s" across the needle and the ground for a given period.

Although the exact mechanism is not understood at this time, the inventor, Dr. M. Yamada surmises that, under the influence of the radicular block, the body undergoes a localized relaxation under the influence of which blood vessels open, circulation increases to high levels and the bodies self-healing function is facilitated in a manner which promotes rapid healing. While the mechanism is not clear, empirical results have shown the technique to be highly effective and to exhibit no undesirable side effects as is often the case with ingestion and/or injection of various known medicines.

In more detail, it is firstly necessary to ascertain what part in spine the source of pain is located. Unless this is done successfully, the treatment will usually be of no avail.

Figure 3:
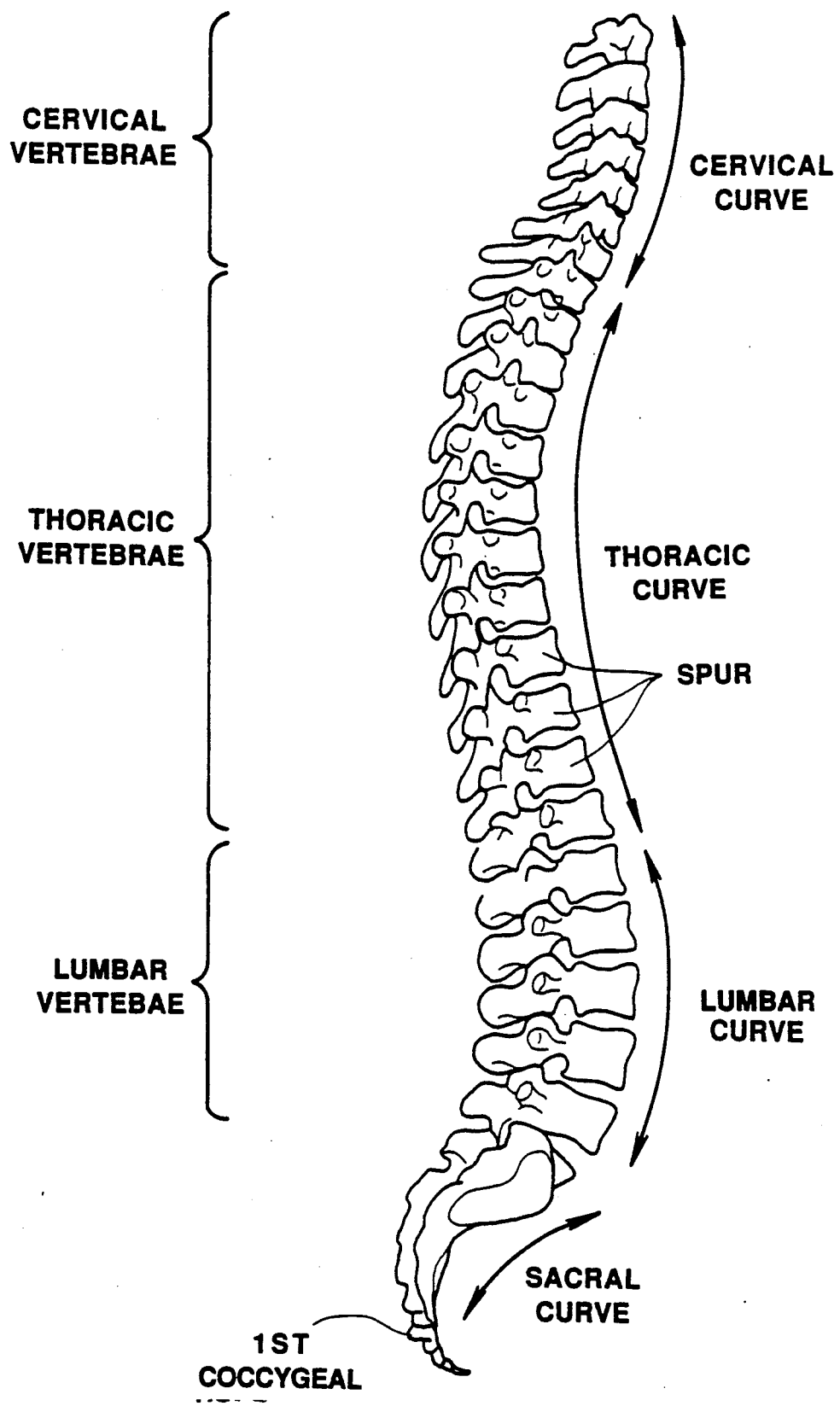
FIG. 3 is a side elevation showing the arrangement of vertebrae in a human vertebral column.
Figure 4:
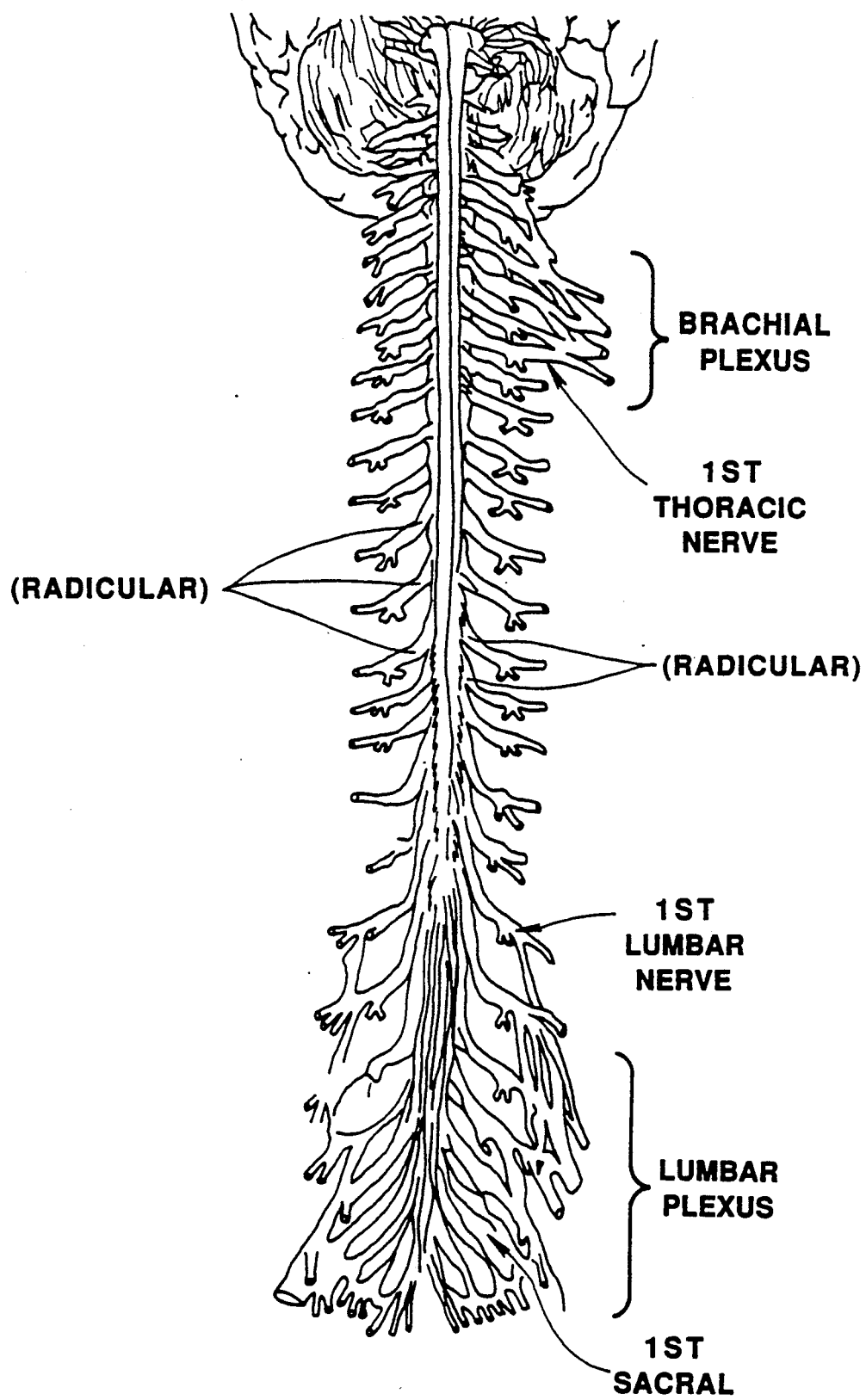
FIG. 4 is a plan view of a human spinal cord which is disposed within the vertebral column.

Assume for the sake of explanation that a source of the pain is located in the lumber region in the area between the 3rd and 4th lumber vertebrae (see FIG. 3).

Upon determination of the source (or sources), the patient should be arranged face down in a comfortably relaxed manner. Following this, a suitably long electrically conductive needle ("n") is inserted and then carefully forced deeper until such time as the radicular in question is penetrated. This penetration will be indicated by a reaction in the patient who will experience an unmistakable reaction to the needle actually penetrating the nerve.

It should be carefully noted at this time that certain regions of the vertebral column, such as the lumber region, are such that the gaps between the spinous processes or spurs of the vertebrae are relatively large (see FIG. 3 and it is possible for the needle to be undesirably inserted into the main body of spinal cord. This should be strictly avoided. With the instant technique, the needle should be inserted in a manner to pierce the radicular which extend from the spinal cord and not the main body of the cord. In the case of the thoracic vertebrae, the spurs tend to be closely located in a manner wherein the above mentioned undesirable center insertion is difficult and tends not to occur. Nevertheless, care should be exercised at all times.

In order to achieve a proper insertion, the needle should be oriented normally to the skin and inserted directly into the body at a site which is located between the spinous process or spur and so that it passes through the depression defined between the ligament between adjacent spinous processes and one of the left or right erector spinae (viz depending on which side of the body is being treated). The needle should be guided so as to avoid contact with a transverse process and until it reaches the radicular. Needless to say, quite a high level of skill is required for this insertion which for the above reasons must be made with care.

In the case of patients who have been afflicted for some time and/or those who are aged, some tissue hardening and/or crystallization is apt to be encountered. Under these conditions, particular care must be exercised in order to achieve the correct needle insertion without causing pain and/or undesired injury.

It also should be noted that the needles used have a diameter which is too small to induce nerve severing. By way of example, needles which can used are commercially available as Chinese Needles #8 or #10. In the case of very large or obese people longer needles may be necessary in order to enable the spinal cord to be reached and penetrated. The above mentioned #8 and #10 needles have an overall length of 11 cm. The upper ends of these needles have enlarged diameter portions suitable for gripping with the fingers and/or electrical connector clips.

From a beginner's point of view, until the instant technique is mastered, it may be advantageous to limit use to Japanese type needles #2-#3.

As those who are skilled in the art of acupuncture will be more than familiar with the Japanese and Chinese types of needles which are commercially available and the manner in which they are used, no further description of the same will be given for brevity.

After the insertion of the "active" needle (as it will be referred to) into the appropriate location, a ground is provided. The preferred manner of providing this ground is to insert a second needle at a location which is about 3-6 cm from the active needle. This enables the site of the earth to be accurately determined and therefore carefully control the flow of current through the body. This technique is useful in the case a number of different nerves are being blocked at the same time.

However, it should be noted that the inventive technique is not limited to the use of needles as an earth, and that in place thereof a metal plate suitably moistened with electrolyte can be placed against the patient's stomach or the like. Alternatively, it is not outside the scope of the present invention that a grounded hand held electrically conductive bar be used as an earth.

Figure 1:
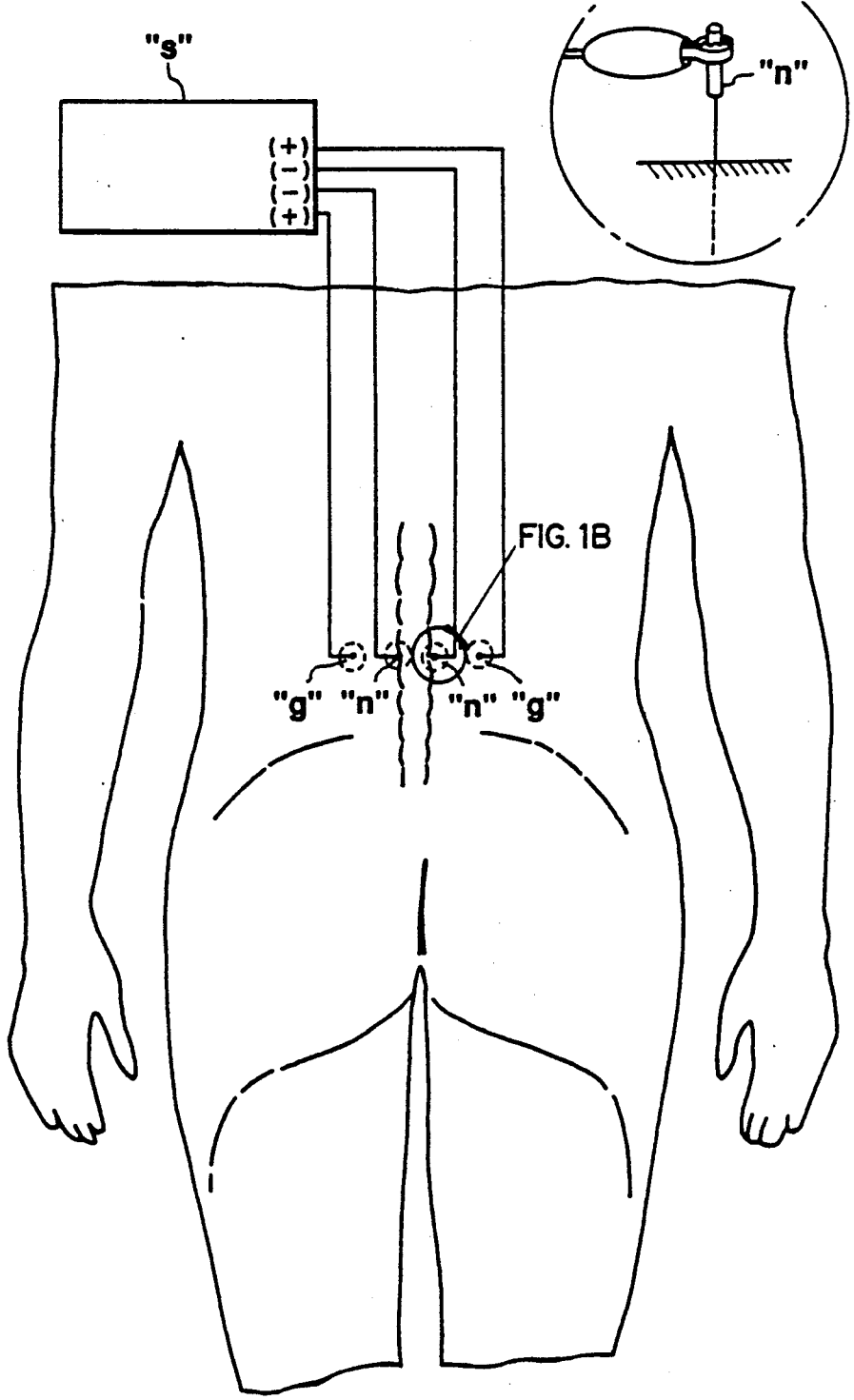
FIG. 1 is a schematic drawing showing a patient undergoing a radicular or nerve root blocking technique which characterizes a first aspect of the inventive techniques.

In the case wherein pain is experienced on both sides of the body, two sets of needles can be inserted—see FIG. 1 for example. The number of needles which need be applied of course varies with the symptoms exhibited by the patient and the number of sites at which nerve blocking is deemed necessary to be carried out.

Following the insertion or insertions, the needles are connected with a source of electrical signal "S". In this instance, the source takes the form of a commercially available unit-Heilung Point Electro Therapy Model HAL 2810. This device is arranged to produce a pulse current (150 volt(p-p) having a frequency of 10-20 Hz) wherein the wave form is exponential, and wherein with a 500 ohm load, a 5 volt 3 mA signal is generated.

The signal is applied to the needles in a manner wherein the negative terminal(s) is applied to the "active" needle or needles which are inserted into the spinal cord and the positive terminal(s) connected to the grounding needle or needles. The level of the signal can be adjusted to meet patient to patient variations and can be periodically increased as the patient becomes accustomed to the current.

The current is applied for a period of 20 to 30 minutes.

During the actual blocking, a slight lowering of the patient's skin temperature was observed, this being possibly attributable the anesthetic type effect which accompanies the blocking. However, at 5 to 10 minutes following the termination of the process, a 2°-3° C. increase in skin temperature was observed using thermographic techniques. This is deemed indicative of greatly increased blood circulation and associated healing activity.

In connection with the insertion of the "active" needle, when a L2-3 insertion is made (viz., an insertion between the second and third lumber verterbrae), the patient will tend to experience a reaction in the thigh region. In the case when a L3-4 insertion is made, a reaction in the calf region may be expected. However, if the insertion is made so as to penetrate close to the L4 vertebrae, a reaction will tend to occur in the extensor muscle group. On the other hand, in the case of a L4-5 insertion, a reaction will normally be experienced in the crotch and/or primary calf region. In the event that an insertion is made between the L5-S1 (fifth lumber-first sacral curve vertebrae) a reaction may be anticipated to occur in the heel or sole region.

The above described radicular block technique can be combined with rehabilitation type exercises and the use of various type of supporters which support the waist region and reduce the load on the area under treatment.

STATISTICAL DATA

Over a 5 year period, a total of 932 patients were treated. Of these, 187 suffered from intervertebral disc hernia. Following treatment using the above described radicular block technique, 158 exhibited good progress and/or recovery, and 13 improved while 16 showed no change. This was deemed indicative that the treatment was 88.1% effective.

SECOND ASPECT

A second aspect of the present invention takes the form of what shall be referred to as laser thermo therapy. This second aspect of the invention is based on the discovery that if a YAG type laser is used and the patient is subject to one or more sequential spot irradiations (which can be likened to needle insertion or acupuncture using a laser needle as it were), a maximum blood flow is observed within 5 minutes of the treatment, while a maximum body temperature tends to be observed up to 90 minutes after the laser treatment.

Figure 2:
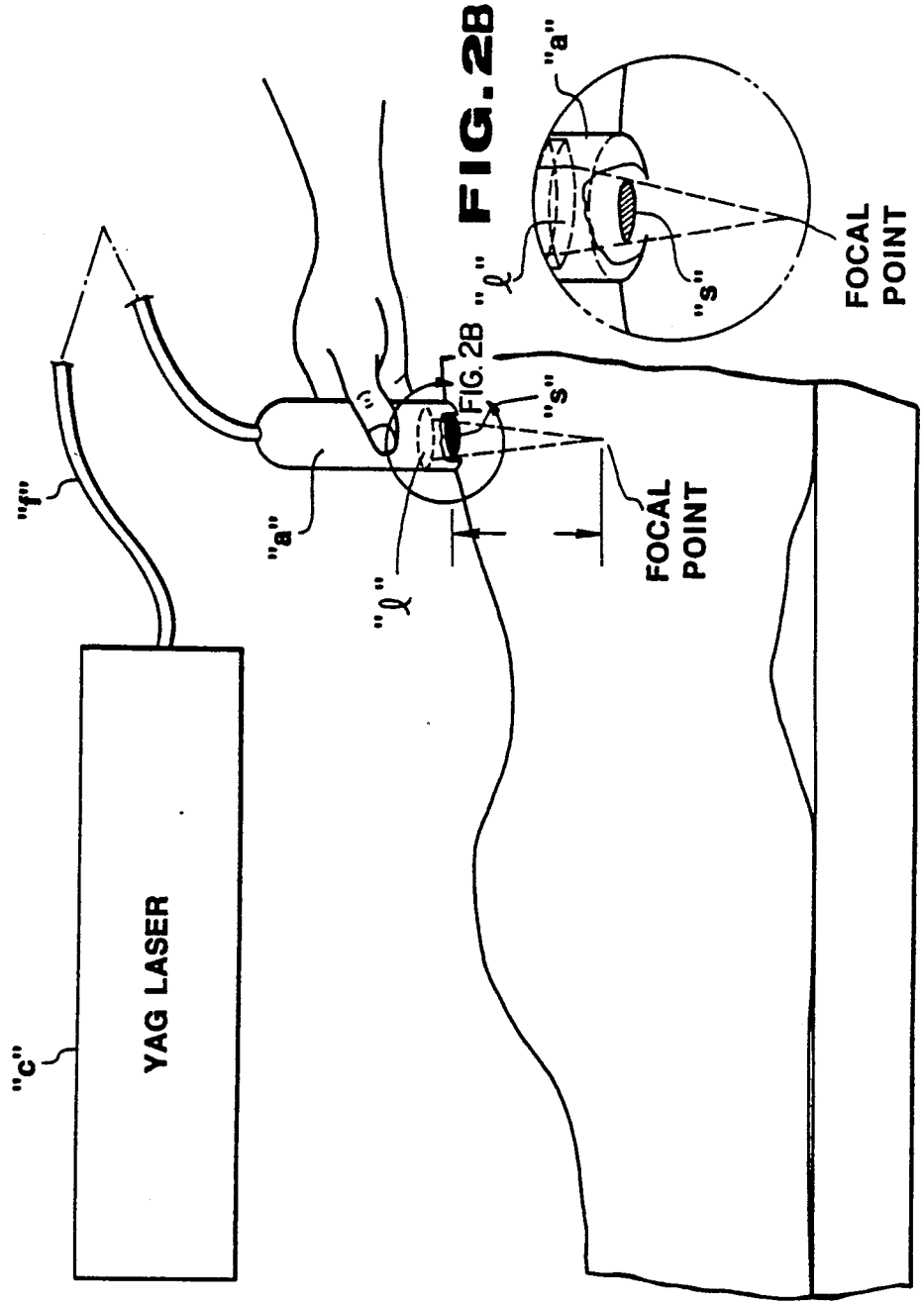
FIG. 2 is a schematic drawing which shows a patient undergoing laser treatment using a YAG type laser in accordance with a second major aspect of the inventive techniques.

In order to shorten the treatment time, a 50 watt YAG laser which is pulsed at one second intervals, is applied in the manner shown in FIG. 2. As will be appreciated from this figure, in order to ensure that the patient is not burned, the laser source is housed in casing "C" which is located adjacent the bed on which the patient is lying, and connected with a hand-held applicator "a" via a light conducting fiber cable "f".

The lens arrangement "l" in the applicator (schematically shown in FIG. 2) is such that the laser is focused at a distance of 10 cm from the end of the applicator. With this arrangement, if the applicator "a" is applied directly against the patient's body, the beam is not focussed and forms a relatively large diameter spot "S" (e.g. 1 cm).

It should be noted that the color of the patient's skin influences the amount of radiation which is absorbed. Light (white) color skin tends to absorb less radiation than darker skin. Thus, the power of the laser should be initially adjusted to lower levels when the patient has dark skin, is tattooed or the like, in order to prevent burning or other discomfort.

It is preferred to use a YAG laser rather than a $CO_2$ or other types. The reason for this selection is that the YAG laser emits radiation in the near infra red zone which is poorly absorbed by the water and red blood cells in the body and tends to be deeply absorbed in the body tissue without causing any undesirable physical side effects. Accordingly, from the view point of efficient use of the radiant energy and simultaneous relative safety, a YAG type laser is deemed to be the most appropriate.

During treatment, the hand held applicator "a" is moved from place to place at 1-2 second intervals. The locations at which and/or the area over which this treatment is conducted of course varies with the symptoms exhibited by the patient and/or the location of the radicular block or blocks if implemented. This procedure is continued until such time as the patient experiences an adequate degree of warming in the area or areas under treatment.

It will be noted that a 1500 mW YAG laser was initially used to irradiate selected spots for 30 seconds. This device took the form of a MNOM and M101MT type YAG laser which was developed with the cooperation of the Nihon Laser Co.

However, the usage of the 1500 mW/30 second laser irradiation technique was later dropped in favour of the above described 50W/1 second technique, as irradiating a large area tended to be time consuming for both the operator and the patient.

The above mentioned 50 W laser is commercially available from the Control Laser Co (of California) as model 512 and from the Nihon Laser KabushikiKaisha (of Japan) as model 706-07.

Tests were conducted with the cooperation of 13 healthy young adult volunteers in order to determine the effect of laser irradiation on blood circulation and the peripheral nervous system.

A Doppler type flow meter was used to detect blood flow changes while a thermograph was used to observe changes in body temperature (as exhibited by skin temperature). After each of the test subjects has stopped moving and had rested quietly for about five minutes, the blood circulation levels assumed stable values. Each of the subjects was then subject to 30 second spot irradiation using a 1500 mW YAG laser.

In the case irradiation was made at a preselected pressure point (so called "saiko") on the forearm of the subject, a maximum blood flow was noted 5 minutes after the irradiation while a marked increase in skin temperature occurred some 90 minutes after. On the other hand, in the cases wherein irradiation was carried out in the lumber 4-5 for a one minute period, after a 20 minute period, the skin temperature of the subject's calves exhibited an increase from 31.4°-32° C. to 32.9°-30.7° C.

The latter mentioned irradiation procedure was conducted with a patient suffering from a intervertebral disc hernia. In this instance, the skin temperature of the patient's calves was observed to change from 27.8°-28° C. to 29.8°-30° C. over a 20 minute period.

From the above results it was deemed that the laser irradiation had a marked effect on circulation and peripheral nervous activity and could be used in connection with the treatment of the above mentioned type of complaint.

STATISTICAL DATA

Over a 15 month period a total of 333 patients were treated using the above described laser treatment. Of these 113 were suffering from ruptured spinal discs. 101 of these patients either recovered or exhibited very marked improvement while 10 showed no change. The remaining 2 were lost contact with and the results of the treatment could not be verified. Statistically, this treatment was considered to be 89.3% effective.

Of the 220 who were not suffering from intervertebral disc hernia, 194 exhibited good recovery and/or were cured while 26 showed no change. The laser treatment with these other complaints was therefore considered to be 88.1% effective.

Merely by way of example, the maladies included in the second group comprised stiff shoulders, rheumatics allergy related nasitis, lumbago, asthma, slipped disc, sprains and the like.

THIRD ASPECT

A third aspect of the present invention is deemed to relate to the combination of the first and second techniques. In other words, firstly execute a radicular block and then follow this with laser treatment. In the instances the two techniques have been combined, the rate of recovery of the patient is increased notably.

What is claimed is:

1. A remedial technique comprising the steps of:
    inserting an acupuncture needle into a preselected radicular of a spinal cord of a patient;
    providing a ground by which electrical current applied to the body of the patient through the acupuncture needle can be grounded; and
    applying a pulsed electrical current across the needle and the ground until the preselected radicular is blocked.

2. A remedial technique as claimed in claim 1 wherein said ground is provided by inserting a second acupuncture needle at a location a given distance from the a said acupuncture needle.

3. A remedial technique as claimed in claim 2 wherein said given distance is selected to be 3-6 cm.

4. A remedial technique as claimed in claim 1 wherein said pulsed electrical current is controlled so as to exhibit a frequency which is from 10-20 Hz.

5. A remedial technique as claimed in claim 4 wherein said pulsed electrical current exhibits an exponential wave form.

6. A remedial technique as set forth in claim 1, further comprising the step of:
   irradiating a predetermined location of a body of a patient proximate the site of the radicular block using a laser beam from a laser for a given length of time.

7. A remedial technique as claimed in claim 6 further comprising the steps of sequentially irradiating a plurality of selected sites on body.

8. A remedial technique as set forth in claim 6, wherein the step of irradiating is carried out by using a YAG type laser to provide said laser beam.

9. A remedial technique as claimed in claim 7, wherein said laser used in said irradiating step is a 50 Watt YAG laser and wherein each site is irradiated for approximately 1 second.

10. A remedial technique as claimed in claim 7, wherein said laser used in said irradiating step is a 1500 mW YAG laser and wherein each site is irradiated for approximately 30 seconds.

11. A remedial technique comprising the steps of:
    inserting an acupunture needle into a preselected radicular of a spinal cord of a patient;
    providing a ground to which electrical current applied to the body of the patient can be grounded; and
    applying a pulsed electrical current across the needle and the ground until the preselected radicular is blocked;
    irradiating a predetermined location of the body of a patient proximate the site of the radicular block using a laser beam for a given length of time; and
    repeating the irradiation at a plurality of other locations until such time as the patient experiences a deep warming sensation over the area under treatment.

12. A remedial technique as set forth in claim 11, wherein the step of irradiating is carried out by using a YAG type laser to provide said laser beam.

* * * * *